United States Patent [19]

Kaplan

[11] Patent Number: 5,120,833
[45] Date of Patent: Jun. 9, 1992

[54] METHOD OF PRODUCING GRAFTS

[76] Inventor: Alexander Kaplan, 22603 66 Ave., W., Mountlake Terrace, Wash. 98043

[21] Appl. No.: 669,920

[22] Filed: Mar. 15, 1991

[51] Int. Cl.$^5$ .......................... A61F 2/06; C07K 3/08
[52] U.S. Cl. ..................... 530/356; 424/423;
514/801; 514/953; 530/402; 600/36
[58] Field of Search ............... 530/354, 356, 402, 812;
514/801, 953; 424/423, 424, 425, 569;
128/DIG. 8; 600/36

[56] References Cited

U.S. PATENT DOCUMENTS

| | | | |
|---|---|---|---|
| 3,106,483 | 10/1963 | Kline et al. | 424/423 |
| 3,514,518 | 5/1970 | Charier-Vardot | 530/356 |
| 4,083,066 | 4/1978 | Schmitz et al. | 3/1.4 |
| 4,167,045 | 9/1979 | Sawyer | 3/1.4 |
| 4,600,533 | 7/1986 | Chu | 530/356 |
| 4,747,848 | 5/1988 | Maini | 530/354 |
| 4,842,575 | 6/1989 | Hoffman, Jr. et al. | 600/36 |
| 4,902,290 | 2/1990 | Fleckenstein et al. | 128/DIG. 8 |
| 4,911,713 | 3/1990 | Sauvage et al. | 623/1 |
| 5,037,377 | 8/1991 | Alonso | 128/DIG. 8 |

OTHER PUBLICATIONS

Guidoin et al., "Collagen coatings as biological sealants for textile arterial protheses", *Biomaterials*, vol. 10, Apr. 1989, pp. 156–165.

Jordan et al., "Gelatin-impregnated Dacron prosthesis implanted into porcine thoracic aorta," Surgery, vol. 53, No. 1, pp. 45–53, Jan. 1963.

*Primary Examiner*—Jeffrey E. Russel
*Attorney, Agent, or Firm*—Cassidy, Vance & Tarleton

[57] ABSTRACT

A unique method (10) for preparing protein-impacted grafts (22) wherein an untreated graft (22) is impacted and impregnated with a protein solution, ideally a collagen suspension (14) utilizing a dynamic flow soaking process (24). After soaking in the dynamic flow (24), the collagen-impacted graft is thermally and chemically fixed (26). Following a water wash (30) and glycine wash (34), the graft (22) is softened with a plastification procedure (36), after which it is air dried (38) and placed in a package and sterilized. With the method of the present invention, storable, surgically-ready collagen-impacted grafts can be reliably and rapidly prepared with a high degree of control and uniformity of characteristics in each graft than has heretofore been possible.

41 Claims, 2 Drawing Sheets

METHOD OF PRODUCING GRAFTS

TECHNICAL FIELD OF THE INVENTION

The present invention is directed to the production of arterial grafts, and, more particularly, to a method of producing storable, surgically-ready protein-impacted grafts.

BACKGROUND OF THE INVENTION

Human blood vessels damaged beyond repair by disease or injury are typically replaced with artificial blood vessels, commonly known as vascular grafts. Most grafts in use today are porous in nature, being typically formed of knitted or woven fibers. However, in order for the porous graft to conduct fluid without leaking, it must be impregnated with a material that ensures hemorrhage-free conduction of blood.

One proposed method for forming an artificial vascular graft is disclosed in U.S. Pat. No. 4,842,575. As taught therein, an aqueous slurry of collagen fibrils is deposited in the lumen of a previously prepared graft and manually massaged to ensure intimate mixing of the collagen into the porous structure of the graft substrate. After massaging, the collagen is dried and cross-linked by exposure to a formaldehyde vapor. This procedure is repeated as necessary to ensure a blood-tight graft. There are numerous drawbacks to grafts produced by this method. First, grafts produced by manual massaging will have an uneven distribution of collagen throughout the graft walls, resulting in uneven porosity. This requires repeated applications by manual massaging, typically six applications, according to the teachings of the patent. In addition, these grafts may have excess collagen deposited throughout the interior wall of the graft, yielding an uneven flow surface. This can result in excess collagen being carried away by the blood flow, and can cause postsurgical complications. Hence, this method lacks the ability to control the internal wall flow surface characteristics and does not provide consistent uniformity in each graft. Because this method is labor intensive, it is slow, inefficient, and unreliable.

Consequently, there is a need for a method of efficiently producing storable, surgically-ready, protein-impacted grafts that enables reliable control over the rate and direction of impaction.

SUMMARY OF THE INVENTION

The present invention is directed to a method of producing a storable, surgically-ready protein-impacted material, ideally a vascular graft. The method comprises the steps of soaking an untreated graft in a flow of protein suspension, preferably a collagen suspension, fixing the collagen in the graft, softening the collagen-impacted graft in a softening solution, and air-drying the protein-impacted graft prior to packaging. While collagen will be used herein as the preferred protein, it is to be understood that the invention has applicability to other proteins, as will be described more fully below.

In accordance with another aspect of the present invention, the step of soaking the graft in a flow of collagen suspension includes the step of preparing a buffer solution comprised of 0.5% to 25% weight/volume (w/v) sodium chloride and 0.5% to 25% w/v sodium acetate in aqueous solution. A collagen suspension is then prepared by mixing 1% to 7% w/v collagen, ideally a Type 1 Bovine Fibrous Collagen with the buffer solution. Preferably, the mixture is blended for at least 4 minutes then set aside until the collagen suspension and foam are separated, after which the collagen suspension is collected. It is to be understood that other proteins may be used, such as 1% to 10% w/v gelatin. In addition, 0.3% to 25% w/v albumin may be added to the collagen, gelatin or a mixture of collagen and gelatin.

In accordance with yet another aspect of the present invention, the step of soaking the graft comprises mounting the graft in a reactive tube and subjecting the graft to a flow of heated water and then to a flow of collagen suspension at an elevated temperature and at a pressure differential between the inside and outside wall surfaces that forces the collagen suspension into the walls of the graft.

In accordance with still yet another aspect of the present invention, the collagen is thermally fixed on the exterior surface of the collagen-impacted graft by placing the graft in a refrigerator or freezer and exposing the graft to subfreezing temperatures to gel the collagen impacted in the graft. Ideally, the graft is placed in the freezer for approximately ten minutes.

In accordance with yet another aspect of the present invention, the collagen is chemically fixed in the collagen-impacted graft by subjecting the graft to a cross linking agent, such as various aldehydes, for a predetermined period of time, preferably by soaking the graft in a formaldehyde solution having a concentration of 0.5% to 20% volume/volume (v/v) for at least one hour.

In accordance with a further aspect of the present invention, the graft is softened by soaking in a solution of alkyl alcohol containing at least two hydroxyl groups, preferably glycerin, for a predetermined period of time, preferably at least one hour. The glycerin can be diluted with water to concentrations exceeding 10% v/v.

In accordance with yet a further aspect of the present invention, after rinsing and soaking in the glycerin solution, the collagen-impacted graft is air-dried for a predetermined period of time, preferably at least 12 hours.

The preferred methodology for such prosthesis may additionally comprise the step of treating the prosthesis with a glycine solution prior to the drying procedure. The glycine solution is preferably a 1% to 10% w/v aqueous solution.

As will be readily appreciated from the foregoing description, the present invention does not require any presoaking of the graft prior to placement in a soaking apparatus. This saves time as well as the cost of the chemicals. Mechanically impacting the graft with a dynamic flow of protein suspension enables more precise control of the amount of protein impregnated in the graft walls. In addition, a smooth inner wall surface of consistent quality is formed in each succeeding graft produced because the process is easily automated. Furthermore, thermal fixation enables soaking the graft in a formaldehyde solution without having the impacted protein washed out. This avoids the use of formaldehyde vapor, which is difficult to work with and requires a special apparatus to treat the materials. Finally, the protein suspension can be used again to treat additional grafts. Accordingly, the present invention provides a controllable, reliable and efficient method of producing protein-impacted grafts with very low water permeability that are storable in a surgically-ready state.

BRIEF DESCRIPTION OF THE DRAWINGS

The foregoing features and advantages of the present invention will be more readily appreciated as the same becomes better understood from the detailed description of the preferred embodiment when taken in conjunction with the following drawings, wherein.

DETAILED DESCRIPTION

In accordance with the method of the present invention, an untreated graft is impregnated with a protein, packaged, and sterilized for later use during surgery. Because these grafts are well known in the art and commercially readily available, they will not be described in detail herein. Briefly, these grafts are typically porous because they are constructed of fibrous material to enhance bonding with living tissue. As a result of this porosity, it is necessary to impregnate the graft with a material that enables the graft to provide a leak-proof conduit for blood. It is to be understood that while the following description denotes certain quantities in connection with the preparation of a protein impregnated graft, these quantities may be varied proportionately to enable preparation of more grafts. In addition, while the following description recites the use of a collagen suspension, it is to be understood that other proteins may be used, such as gelatin, or a mixture of gelatin and collagen. A mixture of albumin with collagen and/or gelatin in predetermined proportions can also be used.

Figure 1:
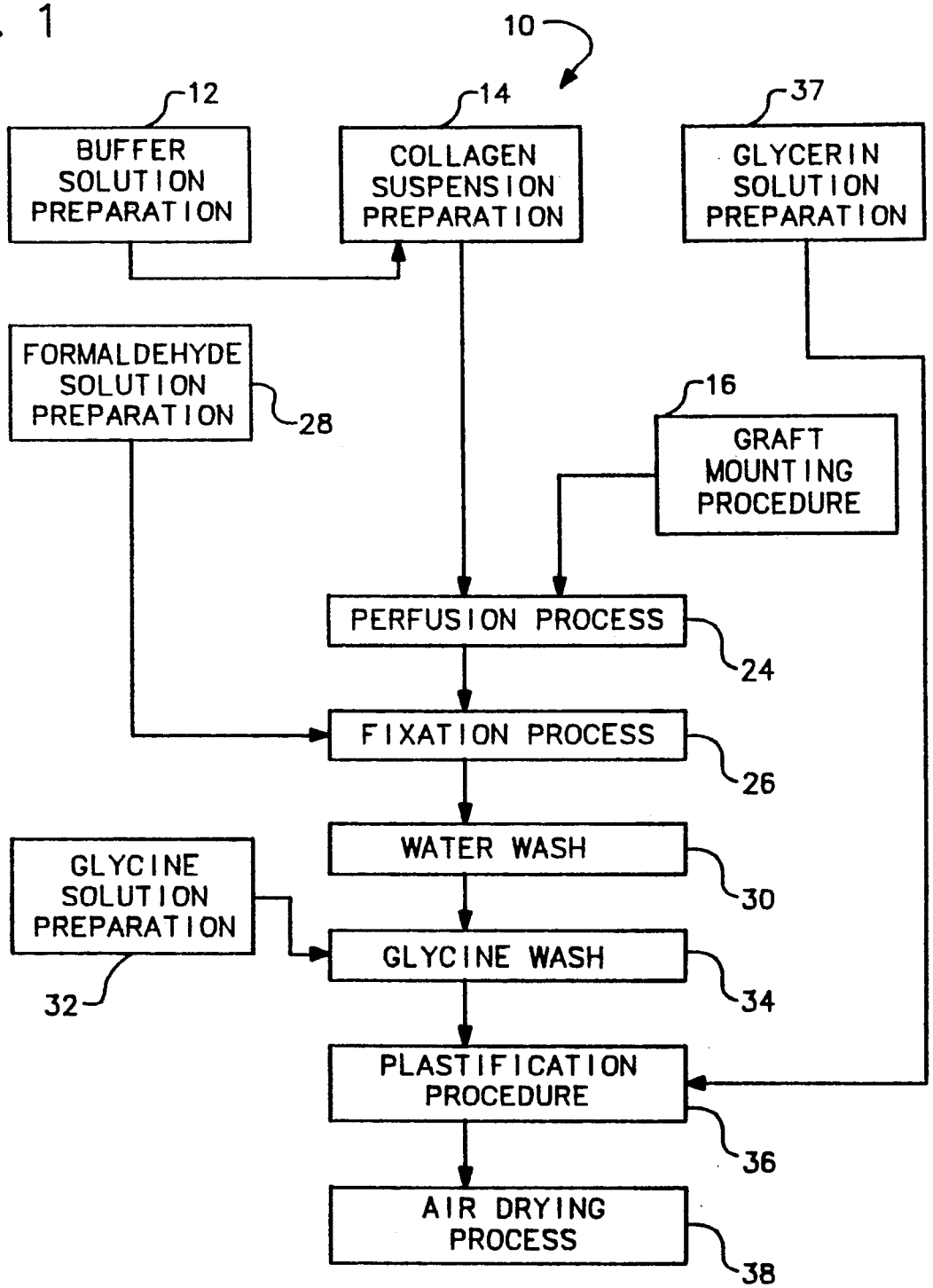
FIG. 1 is a schematic representation of the method of producing a protein-impacted graft in accordance with the present invention.

Referring initially to FIG. 1, in accordance with a preferred method 10 of the present invention of producing a protein-impacted graft, a buffer solution 12 is first prepared. The preparation of the buffer solution 12 requires mixing 0.5% to 25% w/v sodium chloride with 0.5% to 25% w/v sodium acetate in an aqueous solution. This solution can be stored at room temperature for at least a week.

In the next step, a protein suspension 14 is prepared. Ideally, 1% to 7% w/v of Type 1 Bovine Fibrous Collagen is combined in the buffer solution in a blender for at least 4 minutes or until a homogenous suspension is formed. While this may involve an increase in temperature during the mixing or homogenization process, this temperature increase is acceptable.

The collagen suspension is transferred to a beaker and placed in a water bath at 35 to 40 degrees Centigrade. The mixture is left undisturbed for the collagen suspension and foam to separate. When separation is complete, the collagen suspension is collected and placed in another beaker. The collagen suspension can be stored in a sterile environment at 35±10% degrees Centigrade for no more than 48 hours or it can be frozen and liquified before use.

Figure 2:
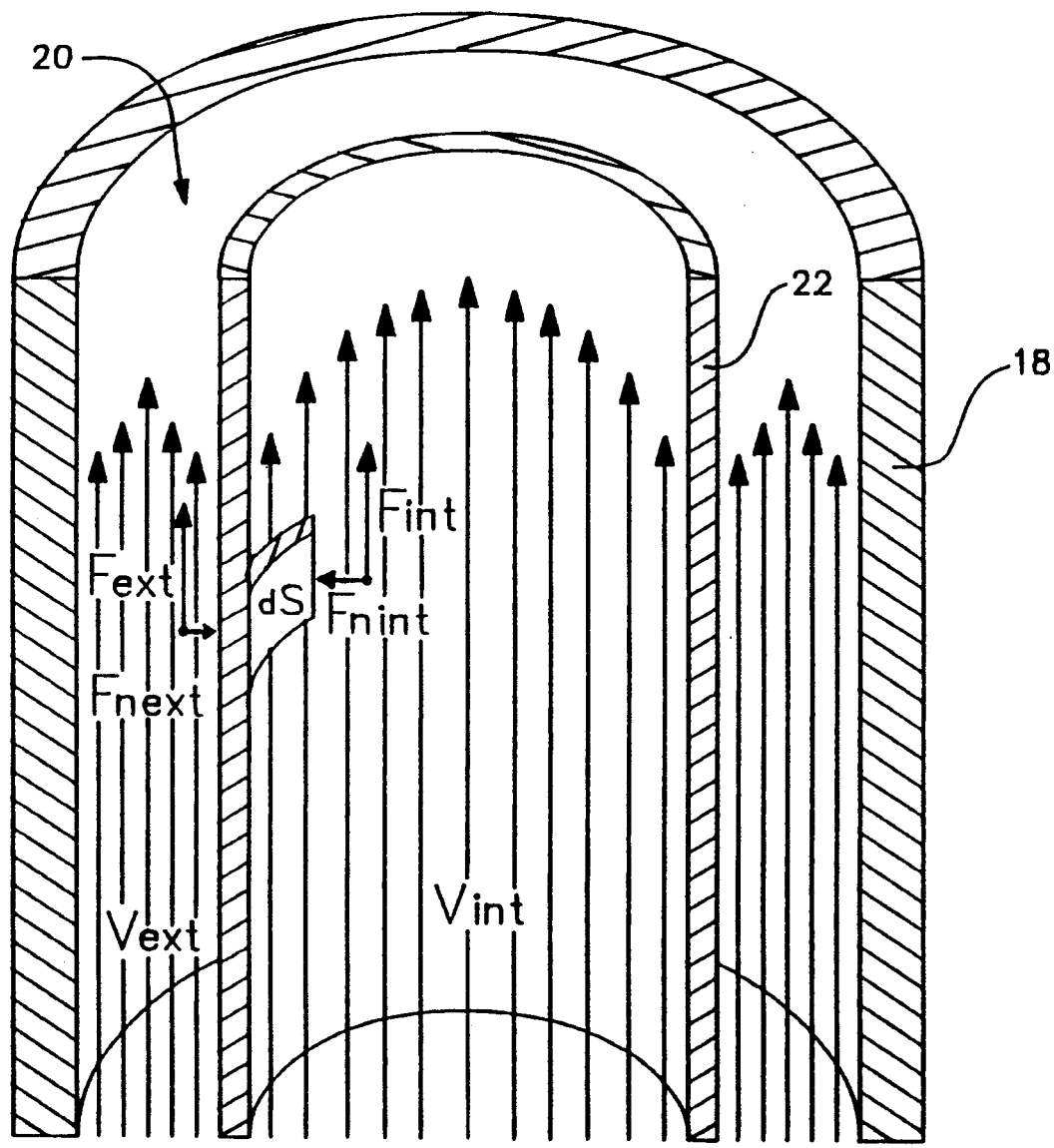
FIG. 2 is a partial cross-sectional view of a graft soaking in a flow of collagen suspension inside a reactive tube.

Mounting 16 and soaking 24 of the graft 22 will now be described in conjunction with FIG. 2. Illustrated in FIG. 2 in cross section is a reactive tube 18 that has a longitudinal axial bore 20. Mounted in the bore 20 is an untreated prosthesis or artificial graft 22, also shown in cross section. Ideally, the graft 22 is a straight graft, 6 or 8 millimeters in diameter, that is readily commercially available and will not be described in detail herein. In the step of mounting 16 the graft 22, one end of the graft 22 is secured so that the graft 22 hangs in a vertical position. Preferably, a 400 gram weight is attached to the free end of the graft 22 to stretch the material of the graft 22. The graft 22 is measured to 35.5 inches from the clamped end and the excess material is detached. Typically, most mechanical perfusion devices can handle up to twelve grafts, which should all be measured and cut in the manner described above.

The internal assembly of the reactive tube 18 is removed from the apparatus and each graft 22 is loaded into a reactive tube 18 according to conventional procedures. The graft 22 and reactive tube 18 are secured back in the apparatus prior to operation.

Initially, water is pumped through the graft to open the pores or interstices of the graft wall. The temperature of the water is held in the range of 50-65 degrees Centigrade. After a predetermined period of time, the water is drained and replaced with the collagen suspension which is heated in the range of 38-40 degrees Centigrade. The graft is soaked in a flow of the previously prepared collagen suspension until it is completely saturated to complete the dynamic soaking process 24. As shown in FIG. 2, the velocity of the internal flow $V_{int}$ of collagen suspension in the graft 22 generates an internal force $F_{int}$ having force component $Fn_{int}$ normal to the interior of the graft wall that is less than the external force component $Fn_{ext}$ normal to the exterior of the graft wall generated by the velocity $V_{ext}$ of an external flow of collagen suspension which forces the suspension into the walls from the inside out. This simulates the flow of blood through the graft and enables control of the quality of the internal wall.

The fixation process 26 comprises two general steps, thermal fixing and chemical fixing. In the thermal fixation process, the collagen-impacted graft is removed from the reactive tube 18 and placed in a freezer where it is exposed to subfreezing temperatures. This causes the exterior of the collagen to gel and thereby hold the collagen in place in the interstices of the graft walls and prevent it from being washed out during the chemical fixation process. Ideally, the graft is exposed to the subfreezing temperatures for approximately ten (10) minutes.

Once thermal fixation is complete, a formaldehyde solution 28 is prepared for the chemical fixation step. The formaldehyde solution preferably has a concentration of 0.5% to 20% v/v in aqueous solution. If necessary, this solution can be stored at room temperature for at least a week. The graft 22 is placed in sufficient formaldehyde solution to completely cover the graft. The graft is permitted to soak for a predetermined period of time, preferably at least one to three hours.

The chemically-fixed collagen-impacted grafts are then removed from the formaldehyde solution and subjected to a water wash 30. This wash is conducted in a laminar flow hood using aseptic technique. The graft is placed in a sterile container and rinsed with sterile water. Enough sterile water is then added to cover the grafts and the container is closed. The grafts then soak for a predetermined period of time, preferably at least one to two hours.

A glycine solution 32 is then prepared consisting of 1% to 10% w/v aqueous solution. The glycine solution should be used within one (1) week after the preparation date. In the glycine wash procedure 34, a laminar flow hood using aseptic technique is used. The washed grafts are placed in a sterile container and the glycine solution is added to cover the grafts. The grafts are rinsed and the solution is drained out of the container. The grafts are then covered with a glycine solution and again allowed to soak, this time for at least one to three hours.

To be sure that all free aldehyde groups are removed during the washing and soaking steps, a sterile syringe is used to draw out approximately a 10 mL sample of the glycine solution, which sample is then checked for the absence of free aldehydes. Assuming the absence of free aldehyde groups, the grafts are then stored in a sterile container.

In the plastification procedure 36, the grafts are first softened by soaking in a glycerin solution. Glycerine solution 37 preparation can be accomplished by mixing glycerin with sterile water. The glycerin solution may be diluted with water to a concentration of at least 10% v/v. This solution can be stored at room temperature for at least a week. The grafts are rinsed with sterile water, placed in a sterile container, and enough glycerin is added to cover the grafts. The grafts are allowed to soak for a predetermined period of time, preferably at least one to three hours.

In the final air drying process 38, the grafts are removed from the glycerin solution and gently shaken to remove residual glycerin. The grafts are then placed in a sterile environment and allowed to air dry for a predetermined period of time, preferably at least ten to twelve hours. After each graft has dried, it is placed in a package for sterilization, and stored.

While a preferred embodiment of the invention has been illustrated and described, it is to be understood that various changes may be made therein without departing from the spirit and scope of the invention. For instance, the glycine wash may be omitted, if desired. In addition, the dynamic soaking process may consist of subjecting the graft to only an internal flow of protein suspension. This will still force the suspension into the graft walls from the inside out. Finally, other porous materials such as flat sheets may be prepared with this method by simultaneously subjecting it to a different flow rate on each side to control the rate and direction of impaction. Consequently, the invention is to be limited only by the scope of the claims that follow.

The embodiments of the invention, in which an exclusive property or privilege is claimed, are as follows:

1. A method of producing a protein-impacted graft, comprising the steps of: soaking an untreated graft in a flow of protein suspension; gelling the exterior surface of the protein-soaked graft by exposing the graft to a subfreezing temperature; fixing the protein in the graft; washing the graft; softening the graft; and drying the graft.

2. The method of claim 1, wherein the step of softening the graft comprises the step of soaking the graft in a softening solution.

3. The method of claim 1, wherein the step of soaking the graft in a flow of protein suspension further includes the step of preparing a suspension of protein.

4. The method of claim 1, wherein the step of washing the graft comprises the steps of washing the graft in sterile water and washing the graft in a chemical solution.

5. A method of producing a collagen graft from an untreated graft that was previously formed of a fibrous material into a tubular shape, comprising the steps of: impacting the untreated graft with a collagen suspension; thermally fixing the collagen-impacted graft by placing the collagen-impacted graft in a subfreezing environment to gel the collagen on the surface of the collagen-impacted graft; chemically fixing the collagen-impacted graft; softening the collagen-impacted graft; and air drying the collagen-impacted graft.

6. The method of claim 5, wherein the step of impacting the graft comprises the step of soaking the graft in a dynamic flow of collagen suspension.

7. The method of claim 5, wherein the step of chemically fixing the collagen-impacted graft comprises soaking the collagen-impacted graft in a formaldehyde solution.

8. The method of claim 7, wherein the collagen-impacted graft is soaked in formaldehyde for at least one hour.

9. The method of claim 8, wherein the step of chemically fixing the collagen-impacted graft includes the further step of soaking the collagen-impacted graft in sterile water.

10. The method of claim 9, wherein the collagen-impacted graft is soaked in sterile water for at least one hour.

11. The method of claim 6, comprising the further step of washing the collagen-impacted graft in a glycine solution.

12. The method of claim 11, wherein the collagen-impacted graft is washed in a glycine solution for at least one hour.

13. The method of claim 12, wherein the step of washing the collagen-impacted graft includes the further step of determining the presence of free aldehydes in the glycine solution after the collagen-impacted graft has been washed.

14. The method of claim 6, wherein the step of softening the collagen-impacted graft comprises soaking the collagen-impacted graft in a glycerin solution.

15. The method of claim 14, wherein the collagen-impacted graft is soaked in said glycerin solution for at least one hour.

16. A method of producing a storable, surgically-ready collagen-impacted graft from an untreated graft, comprising the steps of: preparing a collagen suspension; soaking the untreated graft in a dynamic flow of collagen suspension; thermally gelling the collagen on the surface of the collagen-impacted graft by exposing the graft to a subfreezing temperature; chemically fixing the collagen in the collagen-impacted graft; washing the collagen-impacted graft; soaking the collagen-impacted graft in a softening solution; air drying the collagen-impacted graft; and packaging the collagen-impacted graft.

17. The method of claim 16, wherein said step of preparing a collagen suspension comprises the step of first preparing a buffer solution.

18. The method of claim 17, wherein the step of preparing a buffer solution comprises mixing sodium acetate with sodium chloride in sterile water.

19. The method of claim 18, wherein the ratio of sodium acetate is in the range of 0.5% to 25% w/v and the ratio of sodium chloride is in the range of 0.5% to 25% w/v.

20. The method of claim 19, wherein the step of preparing a suspension of collagen further includes the step of blending type 1 bovine fibrous collagen with the buffer solution in a blender to form a mixture.

21. The method of claim 20, wherein said step of preparing a suspension of collagen includes a further step of separating a collagen suspension from the mixture.

22. The method of claim 20, wherein said step of soaking an untreated graft in a dynamic flow of collagen suspension comprises mounting the graft in an apparatus and subjecting the graft to a longitudinal flow of collagen suspension.

23. The method of claim 22, wherein the step of thermally gelling the collagen on the exterior surface of the collagen-impacted graft comprises placing the collagen-impacted graft in a freezer to expose said graft to subfreezing temperatures.

24. The method of claim 23, wherein the graft is exposed to subfreezing temperatures for a period of time in the range of ten minutes to fifteen minutes.

25. The method of claim 23, wherein the step of chemically fixing the collagen in the collagen-impacted graft comprises the step of preparing a formaldehyde solution.

26. The method of claim 25, wherein the step of preparing the formaldehyde solution comprises the steps of mixing formaldehyde and sterile water.

27. The method of claim 26, wherein the ratio of formaldehyde is in the range of 0.5% to 20% v/v.

28. The method of claim 27, wherein said step of fixing the collagen in the collagen-impacted graft comprises the further step of soaking said thermally-gelled collagen-impacted graft in the formaldehyde solution.

29. The method of claim 28, wherein the graft is soaked in the formaldehyde solution for at least one hour.

30. The method of claim 28, wherein the step of chemically washing the collagen-impacted graft comprises soaking the collagen-impacted graft in sterile water.

31. The method of claim 30, wherein the graft is soaked in sterile water for at least one hour.

32. The method of claim 30, wherein the step of chemically washing the collagen-impacted graft comprises the further step of soaking the graft in a glycine solution.

33. The method of claim 32, wherein the graft is washed for at least one hour.

34. The method claim 33, wherein the step of chemically washing the collagen-impacted graft comprises the further step of testing the glycine solution after the collagen-impacted graft has soaked for the presence of free aldehyde groups.

35. The method of claim 32, wherein said step of softening the collagen-impacted graft comprises a first step of preparing a glycering solution.

36. The method of claim 35, wherein the step of preparing the glycerin solution comprises mixing glycerin in sterile water.

37. The method of claim 36, wherein the concentration of glycerin exceeds 10% v/v.

38. The method of claim 35, wherein said step of softening the collagen-impacted graft comprises the further step of soaking the collagen-impacted grafts in the glycerin solution.

39. The method of claim 38, wherein the graft is soaked in the glycerin solution for at least one hour.

40. The method of claim 38, wherein said step of air drying the collagen-impacted grafts comprises placing the collagen-impacted graft in a sterile environment and allowing to air dry.

41. The method of claim 40, wherein the graft is allowed to dry for at least twelve hours.

* * * * *